(12) United States Patent
Choe et al.

(10) Patent No.: US 6,907,791 B2
(45) Date of Patent: Jun. 21, 2005

(54) METHODS AND SYSTEMS FOR DETERMINING FATIGUE USAGE FACTORS FOR REACTOR COMPONENTS

(75) Inventors: Hwang Choe, San Jose, CA (US); Betty Jane Branlund, Portola Valley, CA (US); Bettadapur Narayanarao Sridhar, Cupertino, CA (US)

(73) Assignee: General Electric Company, Schenectady, NY (US)

( * ) Notice: Subject to any disclaimer, the term of this patent is extended or adjusted under 35 U.S.C. 154(b) by 311 days.

(21) Appl. No.: 10/280,160

(22) Filed: Oct. 25, 2002

(65) Prior Publication Data

US 2004/0079164 A1 Apr. 29, 2004

(51) Int. Cl.$^7$ .......................... G01N 3/00; G01N 11/00
(52) U.S. Cl. ................................ 73/794; 73/788
(58) Field of Search .................. 73/794, 796, 849, 73/788

(56) References Cited

PUBLICATIONS

ASME Boiler and Pressure Vessel Code, The American Society of Mechanical Engineers, 1989, pp. 77, 79, 80, 81, FIG. I–9.2.1 and FIG. I–9.1.

*Primary Examiner*—Edward Lefkowitz
*Assistant Examiner*—Lilybett Martir
(74) *Attorney, Agent, or Firm*—Armstrong Teasdale, LLP

(57) ABSTRACT

A method for calculating a fatigue usage factor of a component in a nuclear reactor includes determining a flow scaling factor for each stress component of a stress cycle, applying the flow scaling factor to rapid cycling stress conditions, and performing a fatique evaluation by calculating a fatigue usage factor using the flow scaling factor. The flow scaling factor is a ratio of a temperature fluctuation ratio at a first reactor operating condition divided by a temperature fluctuation ratio at a second reactor operating condition. The temperature fluctuation ratio is defined as a ratio of the metal temperature range over the fluid temperature range.

12 Claims, 4 Drawing Sheets

METHODS AND SYSTEMS FOR DETERMINING FATIGUE USAGE FACTORS FOR REACTOR COMPONENTS

BACKGROUND OF THE INVENTION

This invention relates generally to nuclear reactors and more particularly, to a method for reducing the usage factor of the feedwater nozzle in a nuclear reactor.

A reactor pressure vessel (RPV) of a boiling water reactor (BWR) typically has a generally cylindrical shape and is closed at both ends, e.g., by a bottom head and a removable top head. A core assembly is contained within the RPV and includes the core support plate, fuel bundles, control rod blades and a top guide. A core shroud typically surrounds the core assembly and is supported by a shroud support structure. Particularly, the shroud has a generally cylindrical shape and surrounds both the core plate and the top guide. There is a space or annulus located between the cylindrical reactor pressure vessel and the cylindrically shaped shroud.

Internal structures of operating BWRs are susceptible to various corrosive and cracking processes. Stress corrosion cracking (SCC) is one known phenomenon occurring in reactor components, such as structural members, piping, control rod guide tubes, fasteners, and welds, exposed to high temperature water. The reactor components are subject to a variety of stresses associated with, for example, differences in thermal expansion, the operating pressure needed for the containment of the reactor cooling water, and other sources such as residual stresses from welding, cold working and other inhomogeneous metal treatments. In addition, water chemistry, welding, heat treatment and radiation can increase the susceptibility of metal in a component to SCC.

Most BWR pressure vessels include at least one feedwater nozzle which connect feedwater spargers with the feedwater supply. Feedwater nozzles usually include a thermal sleeve and a safe end which couples to the feedwater supply line. Feedwater is distributed through the spargers that deliver the flow of water to the reactor core to help maintain proper reactor water level. Feedwater nozzle cracking can be caused by thermal fatigue. The thermal fatigue can be caused by a high cycling mechanism which involves rapid temperature cycling and usually initiates the cracking. Also, a low cycle mechanism which is due to changes in the feedwater or reactor water flow temperature can cause the formed cracks to propagate.

Rapid temperature cycling can be caused by leakage flow passing the thermal sleeve and safe end seals. This leakage flow mixes in a turbulent manner with hot downcomer flow in the annulus between the nozzle and the thermal sleeve. The fluid impinges on the nozzle wall before cold and hot water mixes completely and exposes the metal surface to cold and hot water alternatingly, causing thermal cycling of the metal surface. This metal temperature cycling can have a magnitude of up to 50 percent of the difference in temperature between the feedwater and the downcomer water. The metal temperature cycling can have frequencies of between 0.1 and 1.0 Hz and can rapidly initiate cracking. Rapid temperature cycling can also be caused, in the absence of leakage flow, by turbulent downcommer flow causing the thermal boundary layer around the cold thermal sleeve to be broken up intermittently, exposing the nozzle to the alternating cold and hot water streams. Incompletely mixed sparger discharge flow and downcommer fluid carried back to the nozzle also causes some rapid cycling.

BRIEF DESCRIPTION OF THE INVENTION

In one aspect, a method for calculating a fatigue usage factor of a component in a nuclear reactor is provided. The method includes determining a flow scaling factor for each stress component of a stress cycle, applying the flow scaling factor to rapid cycling stress conditions, and performing a fatigue evaluation by calculating a fatigue usage factor using the flow scaling factor. The flow scaling factor is a ratio of a temperature fluctuation ratio at a first reactor operating condition divided by a temperature fluctuation ratio at a second reactor operating condition. The temperature fluctuation ratio is defined as a ratio of the metal temperature range over the fluid temperature range.

In another aspect, a method for scaling stresses in nuclear reactor components to account for changes in reactor operating conditions is provided. The method includes determining a flow scaling factor for each stress component of a stress cycle, and applying the flow scaling factor to rapid cycling stress conditions. The flow scaling factor is a ratio of a temperature fluctuation ratio at a first reactor operating condition divided by a temperature fluctuation ratio at a second reactor operating condition. The temperature fluctuation ratio is defined as a ratio of the metal temperature range over the fluid temperature range.

In another aspect, an apparatus for calculating a fatigue usage factor of a component in a nuclear reactor is provided. The apparatus includes a processor programmed to determine a flow scaling factor for each stress component of a stress cycle, apply the flow scaling factor to rapid cycling stress conditions, and perform a fatigue evaluation by calculating a fatigue usage factor using the flow scaling factor. The flow scaling factor is a ratio of a temperature fluctuation ratio at a first reactor operating condition divided by a temperature fluctuation ratio at a second reactor operating condition. The temperature fluctuation ratio is defined as a ratio of the metal temperature range over the fluid temperature range.

A system for calculating a fatigue usage factor of a component in a nuclear reactor is provided. The system includes a client system having a browser, a data storage device for storing information relevant to a plurality of users, and a server system configured to be coupled to the client system and the data storage device. The server system is further configured to determine a flow scaling factor for each stress component of a stress cycle, apply the flow scaling factor to rapid cycling stress conditions, and perform a fatigue evaluation by calculating a fatigue usage factor using the flow scaling factor. The flow scaling factor is a ratio of a temperature fluctuation ratio at a first reactor operating condition divided by a temperature fluctuation ratio at a second reactor operating condition. The temperature fluctuation ratio is defined as a ratio of the metal temperature range over the fluid temperature range.

DETAILED DESCRIPTION OF THE INVENTION

A method for determining a usage factor of a component in a reactor is described below in detail. Because of safety concerns, reactors have been licensed to operate at a maximum power that is less than what the reactor is capable of producing. From years of reactor operation it has been determined that the safety margins that have limited maximum reactor power output are larger than what are needed for safe reactor operation. As a result, reactors are being reconfigured to operate at higher maximum power. This extended power uprate (EPU) of reactors requires a new license from the governing nuclear regulatory agency. To obtain a license to operate a reactor at higher maximum power, a revised safety analysis report is required where the systems and components of the reactor are analyzed to determine if safe operation is obtainable at the extended power uprate. One of the components that is analyzed is the feedwater nozzles of the reactor. Particularly, an analysis is made of the reactor components to determine if the requirements of the American Society of Mechanical Engineers (ASME) Boiler and Pressure Vessel Code, Section III, Subsection NB, Fatigue Requirements are met. The suitability of a component for specified service loadings involving cyclic application of loads and thermal conditions is determined by calculating a usage factor as defined by the ASME Code. A usage factor larger than one requires an extended Fatigue Monitoring Program at high costs and extended reactor downtime. Typically, conservative techniques are employed using conservative assumptions to calculate the usage factor for a reactor component, for example a feedwater nozzle.

The method for calculating a usage factor described below employs less conservative, but more realistic, assumptions developed from analyses, experimental results, and measurements. The use of the method can result in significant savings by reducing the amount of fatigue monitoring that is required to meet regulatory licensing requirements.

Figure 1:
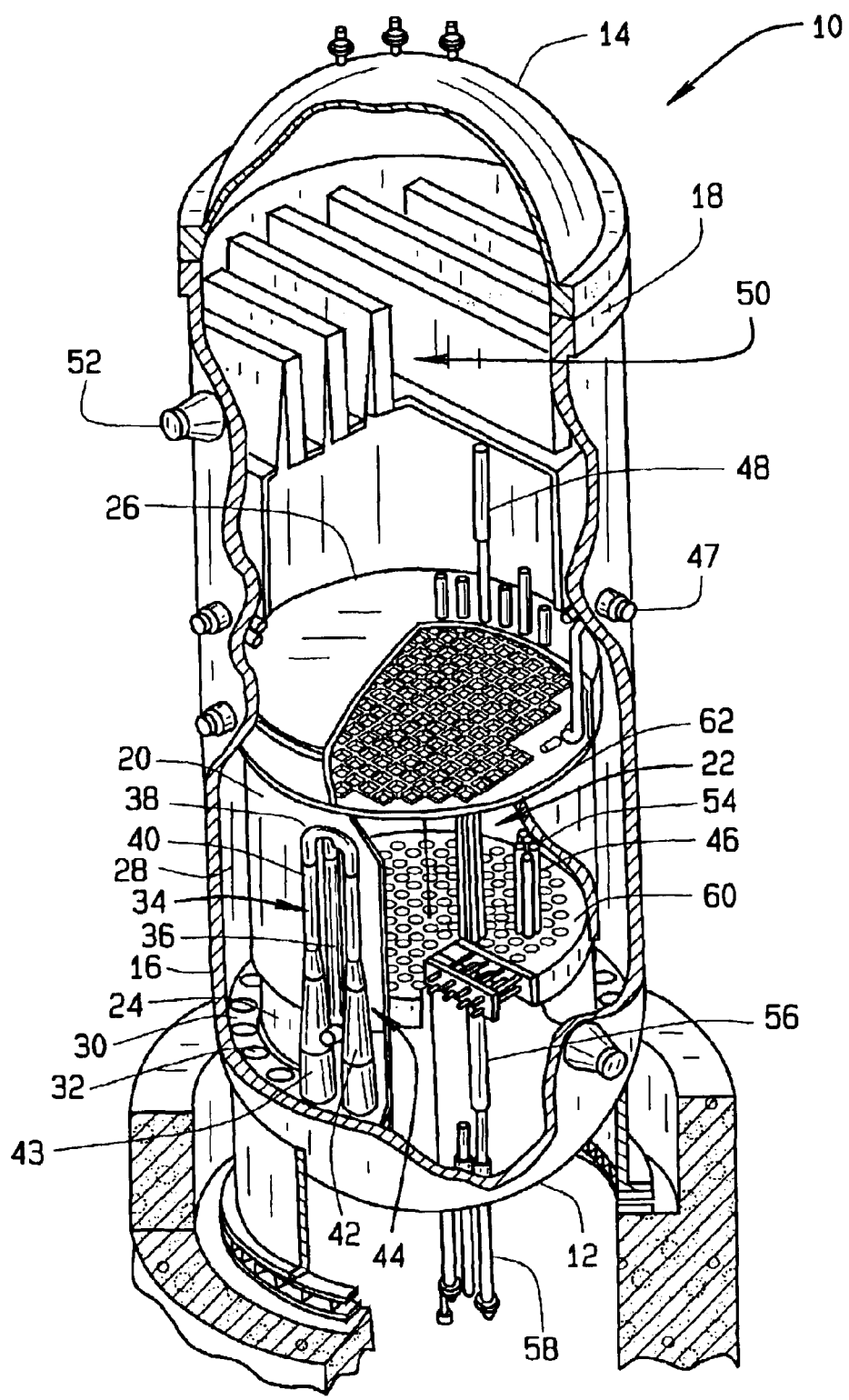
FIG. 1 is a sectional view, with parts cut away, of a boiling water nuclear reactor pressure vessel.

Referring to the drawings, FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes a removable shroud head 26 at the other end. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, a diffuser 42, and a tailpipe assembly 43. Inlet riser 36 and two connected jet pumps 34 form a jet pump assembly 44.

Thermal power is generated within core 22, which includes fuel bundles 46 of fissionable material. Water circulated up through core 22 is at least partially converted to steam. Feedwater enters RPV 10 through feedwater nozzle 47. Steam separators 48 separates steam from water, which is recirculated. Residual water is removed from the steam by steam dryers 50. The steam exits RPV 10 through a steam outlet 52 near vessel top head 14.

The amount of thermal power generated in core 22 is regulated by inserting and withdrawing control rods 54 of neutron absorbing material, such as, for example, boron carbide. To the extent that control rod 54 is inserted into core 22 between fuel bundles 46, it absorbs neutrons that would otherwise be available to promote the chain reaction which generates thermal power in core 22. Control rod guide tubes 56 maintain the vertical motion of control rods 54 during insertion and withdrawal. Control rod drives 58 effect the insertion and withdrawal of control rods 54. Control rod drives 58 extend through bottom head 12.

Fuel bundles 46 are aligned by a core plate 60 located at the base of core 22. A top guide 62 aligns fuel bundles 46 as they are lowered into core 22. Core plate 60 and top guide 62 are supported by core shroud 20.

Figure 2:
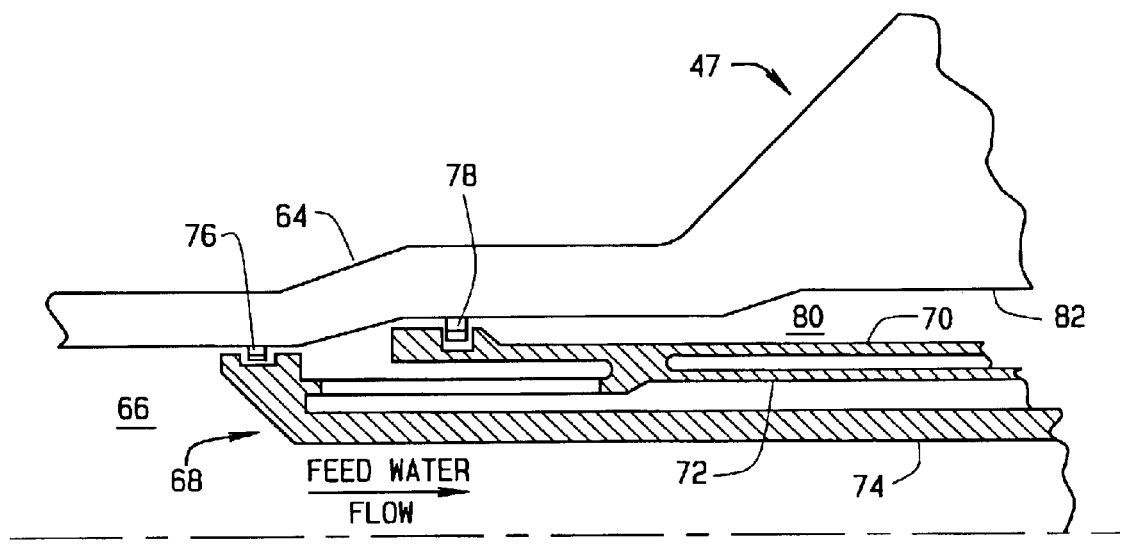
FIG. 2 is a sectional view of a feedwater nozzle shown in FIG. 1.

FIG. 2 is a sectional view of feedwater nozzle 47 which includes a nozzle safe end 64 and a bore 66 extending through nozzle 47. A thermal sleeve 68 is positioned inside bore 66 of feedwater nozzle 47. Thermal sleeve 68 includes an outer thermal sleeve 70, a mid-thermal sleeve 72, and an inner thermal sleeve 74. A primary seal 76 and a secondary seal 78 prevent feedwater from leaking into an annulus space 80 between thermal sleeve 68 and an inner surface 82 of feedwater nozzle 47.

Figure 3:
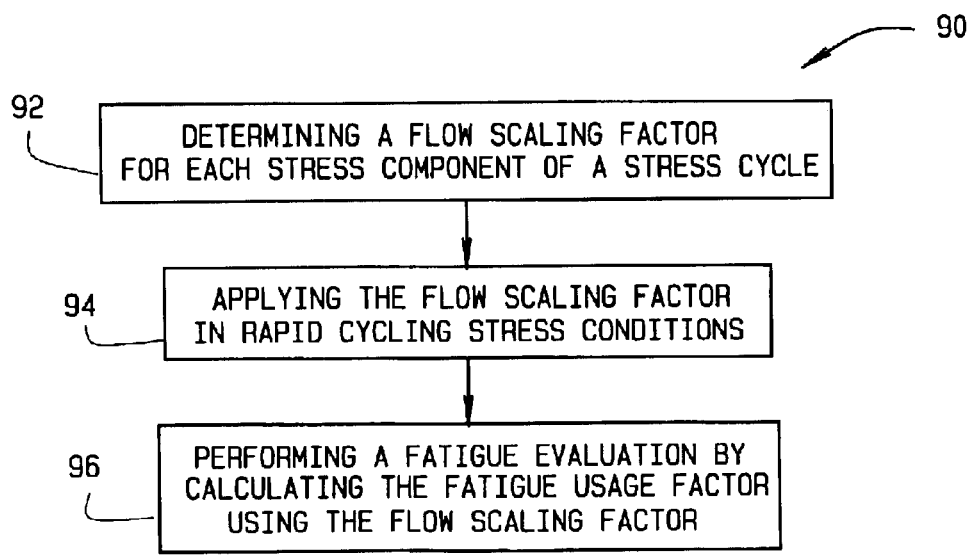
FIG. 3 is a flow chart of a method for calculating the fatigue usage factor of a reactor component in accordance with an embodiment of the present invention.

FIG. 3 is a flow chart of a method 90 for calculating the fatigue usage factor of a reactor component. Method 90 includes determining 92 a flow scaling factor for each stress component of a stress cycle, applying 94 the flow scaling factor in rapid cycling stress conditions, and performing 96 a fatigue evaluation by calculating the fatigue usage factor using the flow scaling factor.

Many pressure vessel calculations select the three stress directions of the orthogonal coordinate system such that the shear stress components are zero and the normal stress components are the principal stresses. With this orientation, the pressure stresses are directly proportional to the increase in coolant pressure, and the magnitude of the principal stress resulting from thermal cycling is proportional to the temperature change during a thermal transient. When there are no changes in mechanical loads as a result of the EPU, the new magnitude of the principal stress is:

$$\sigma_{new} = \sigma_p^*(P_{new}/P_{old}) + \sigma_t^*(\Delta T_{M,new}/\Delta T_{M,old}) + \sigma_m; \quad (1)$$

where, $\sigma_p$=Original Pressure Stress;
 $\sigma_T$=Original Thermal Stress;
 $\sigma_m$=Original Mechanical Stress;
 $P_{new}$=EPU Pressure;
 $P_{old}$=Original Pressure;
 $\Delta T_{M,new}$=EPU Temperature Range of the metal surface; and
 $\Delta T_{M,old}$=Original Temperature Range of the metal.
Equation 1 can be rewritten as:

$$\sigma_{new} = \sigma_p^* SCF_p \sigma T^* SCF_T^* SCF_f + \sigma_m; \quad (2)$$

where, $SCF_p$=Pressure Stress Scaling Factor=$P_{new}/P_{old}$;
 $SCF_T$=Fluid Temperature Stress Scaling Factor=$\Delta T_{f,new}/\Delta T_{f,old}$;
 $SCF_f$=Flow Scaling Factor=$(\Delta T_M/\Delta T_f)_{new}/(\Delta T_M/\Delta T_f)_{old}$;
 $\Delta T_M$=Temperature Range of the Metal; and
 $\Delta T_f$=Temperature Range of the Fluid.

Components that experience a change in internal coolant flow during operation have a flow scaling factor, $SCF_f$. The magnitude of the internal flow changes the convective heat transfer coefficient and the mechanism of transferring the temperature fluctuation from the fluid to the metal. In determining the $SCF_f$, it is known that thermal stress ($\sigma_T$) can be expressed as:

$$\sigma_T=(E\alpha\Delta T_M)/(1-v); \tag{3}$$

where, E=Young's Modulus of Elasticity of metal;
α=Coefficient of Thermal Expansion of metal; and
v=Poisson's Ratio.

Analysis of an oscillating fluid temperature field adjacent to the metal surface has shown that:

$$\Delta T_M/\Delta T_f=1/SQRT(1+2a+2a^2); \tag{4}$$

$$\text{where, } a=SQRT(\pi f\rho CK)/h; \tag{5}$$

π=3.14159;
f=Frequency of Oscillation;
ρ=Density of metal;
C=Specific Heat of metal
K=Thermal Conductivity of metal; and
h=Heat Transfer Coefficient.

Also, it is known for turbulent flow that:

$$N_u=(hD)/K_f=C_fP_r^{1/3}R_e^{0.8}; \text{or}$$

$$h=(C_f/D)K_fP_r^{1/3}(V^{0.8}D^{0.8})/v^{0.8}; \tag{6}$$

where, $N_u$=Nusselt Number (hD)/$K_f$;
$C_f$=Correlation Constant
$P_r$=Prandtl Number;
$R_e$=Reynolds Number=VD/v;
D=Pipe Diameter;
V=Fluid Velocity; and
$K_f$=Fluid Thermal Conductivity.

Applying the above equations in an example nuclear reactor from available measurements it was determined that $\Delta T_M/\Delta T_f$ from equation (4) is 0.5 at pre-EPU flow conditions. Therefore, $1/(1+2a+2a^2)=0.25$, and a=0.8229. Instead of equations (4), (5), and (6), and assuming that $SCF_f$ is directly proportional to the heat transfer coefficient, h, alone, the EPU flow scaling factor $SCF_f$ was calculated conservatively as follows:

$$SCF_f=h_{new}/h_{old}=(EPU \text{ flow/Pre-}EPU \text{ flow})^{0.8}=(9200/7410)_{0.8}=1.189.$$

However, while this assumption is conservative, the $SCF_f$ should be proportional to the ratio, $\Delta T_M/\Delta T_f$, and not the ratio of the heat transfer coefficent alone. Therefore, using equations (4), (5), and (6), $SCF_f$ can be correctly calculated as follows. First, $a_{new}$ at EPU conditions is calculated. Because $a_{new}$ and $a_{old}$ is inversely proportional to $h_{new}$ and $h_{old}$, $a_{new}=a_{old}/(h_{new}/h_{old})=0.8229/1.189=0.6921$.

$$(\Delta T_M/\Delta T_f)_{new}=1/(SQRT(1+2a_{new}+2a_{new}^2));$$

$$(\Delta T_M/\Delta T_f)_{new}=1SQRT(1+2\times0.6921^2+2\times0.6921^2)=0.5470;$$

and $$(\Delta T_M/\Delta T_f)_{old}=0.5.$$

Hence, the revised flow scaling factor $SCF_f$ in accordance with the exemplary embodiment of the present invention, is calculated as:

$$SCF_f=(\Delta T_M/\Delta T_f)_{new}/(\Delta T_M/\Delta T_f)_{old}=0.5470/0.5=1.094$$

Figure 4:
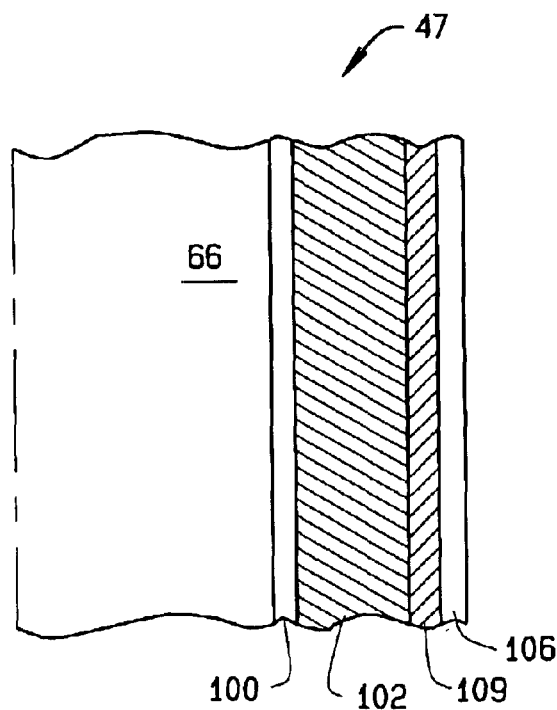
FIG. 4 shows a longitudinal section of the feedwater nozzle shown in FIG. 1.

FIG. 4 shows a longitudinal section of feedwater nozzle 47. Nozzle bore 66 includes a fluid thermal layer 100 which is surrounded by a nozzle wall 102, thermal insulation 104 and an air film 106. The heat transfer coefficients of insulation 104 and air film 106 are several orders of magnitude lower than that of fluid thermal layer 100. For example, typical values of these thermal parameters are:

U=Effective heat transfer coefficient of insulation=0.2 BTU/(hr - $ft^2$-° F.);
$h_f$=Heat transfer coefficient of water film=200 BTU/(hr - $ft^2$-° F.);
$h_a$=Heat transfer coefficient of air film=5 BTU/(hr - $ft^2$ -° F.); and
K=Thermal conductivity of carbon steel pipe=25 BTU/(hr - $ft^2$ -° F.).

During system cycling, the time duration of the transients are much longer than those during rapid cycling. As a result, system cycling is more similar to steady state i.e., all four areas shown in FIG. 4, experience essentially no change in temperature distribution as a result of EPU. A change in the flow within the thermal sleeve has an insignificant effect on the overall heat transfer coefficient and hence thermal stresses of all four areas. Thus, the flow scaling factor for system cycling in the example nuclear reactor is 1.0, or, $SCF_f$ (system cycling)=1.0.

Rapid cycling is, however, a different phenomenon. Time durations are shorter, the metal temperature fluctuation lags behind the fluid temperature fluctuation, and the ratio, $(\Delta T_M/\Delta T_f)$, changes as a function of fluctuation frequency and thermal hydraulic conditions. Any change in the flow significantly affects the heat transfer coefficient of the water thermal layer and hence, the flow scaling factor and the thermal stresses on the FW nozzle. Thus, for rapid cycling in the example nuclear reactor, the flow scaling factor $SCF_f$ is 1.094, instead of a conservatively calculated 1.189, as calculated above in accordance with the exemplary embodiment of the invention.

Performing 96 a fatigue evaluation for EPU conditions in a reactor includes determining the applicable scaling factors for each stress component of the stress cycle, including pressure, temperature and flow scaling factors, and applying the appropriate scaling factor to the corresponding stress components of the stress cycle. The fatigue evaluation includes determining the alternating stress intensity, $S_{alt,new}$, then calculating and applying the correct fatigue strength correction factor, $K_{e,new}$ and elastic modulus correction factor, $E_c/E_a$. The $S_{alt,new}$ for EPU conditions takes the form:

$$S_{alt,new}=(1/2)*K_{e,new}*E_c/E_a*S_{p-p}; \tag{7}$$

where, $S_{alt,new}$=Alternating Stress Intensity at EPU condition;
$K_{e,new}$=Fatigue Strength Correction Factor at EPU condition (defined in ASME code, Section III, §NB-3228.5);
$E_c$=Young's Modulus of elasticity used in ASME fatigue curve;
$E_a$=Young's Modulus of elasticity used in application; and
$S_{p-p}$=The stress range from the maximum peak to minimum valley.

Using $S_{alt,new}$, determine the allowable number of cycles, N, from the fatigue curve appropriate to the material of the component. The above steps are repeated for each peak stress intensity corresponding to a group of cycles considered in the fatigue analysis. The cumulative fatigue usage factor is determined from the formula:

$$U = u_1 + u_2 + \ldots + u_x; \qquad (8)$$

where, $u_x = n_x/N_x$, the incremental fatigue usage factor;

$n_x$=expected number of lifetime cycles experienced by the component; and $N_x$=allowable number of cycles.

Figure 5:
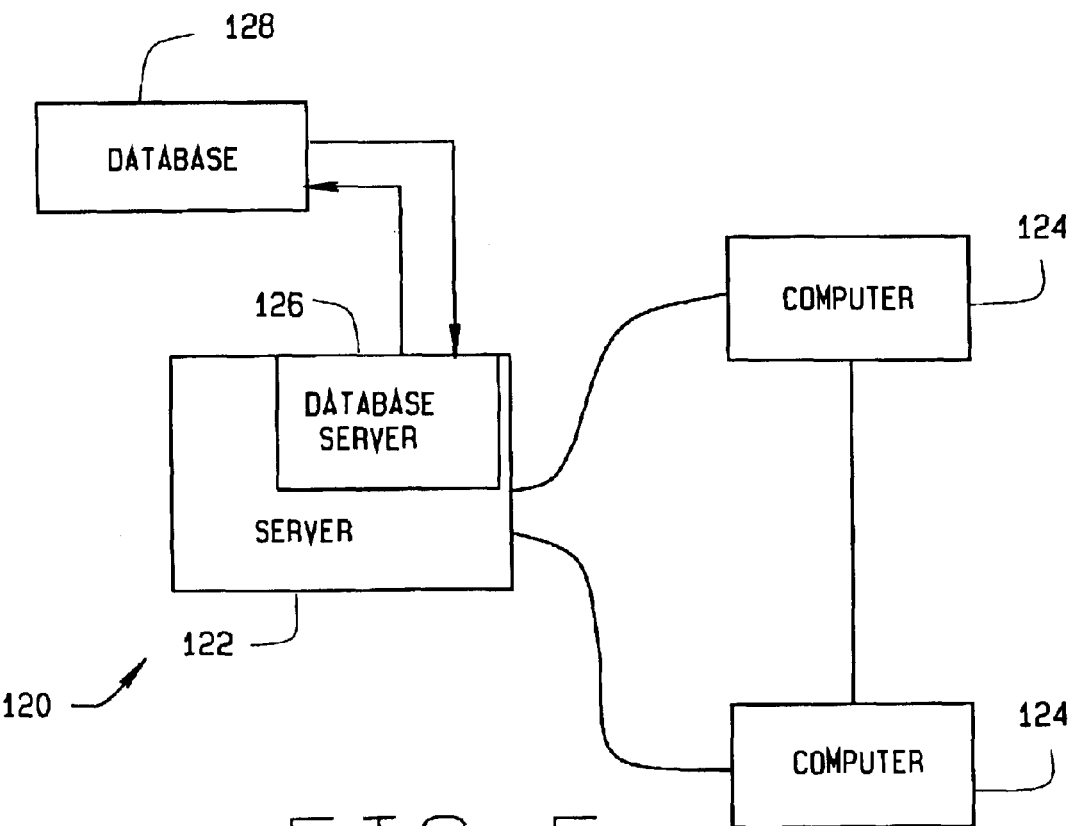
FIG. 5 is a block diagram of a system for determining the fatigue usage factor of a reactor component.

FIG. 5 is a block diagram of a system 120 for determining a fatigue usage factor of a component in a nuclear reactor. System 120 includes a server 122 and a plurality of devices 124 connected to server 122. In one embodiment, devices 124 are computers including a web browser, and server 122 is accessible to devices 124 via the Internet. In an alternative embodiment, devices 124 are servers for a network of customer devices. System 120 is coupled to a mass storage device (not shown). In the exemplary embodiment, server 122 includes a database server 126 coupled to a centralized database 128.

Devices 124 are interconnected to the Internet through many interfaces including through a network, such as a local area network (LAN) or a wide area network (WAN), through dial-in-connections, cable modems and special high-speed ISDN lines. Alternatively, devices 124 could be any device capable of interconnecting to the Internet including a web-based phone or other web-based connectable equipment. A database providing information relating to the plurality of plants is stored on server 122 and can be accessed by users at one of devices 124 by logging onto server 122 through one of devices 124.

System 120 is configured to provide various user interfaces whereby users enter data. Server 122 accesses stored information and downloads the requested operational data to at least one of the client systems 124, when the request to download is received from client system 124. The databases are accessed by users using client system 124 configured with a standard web browser.

Figure 6:
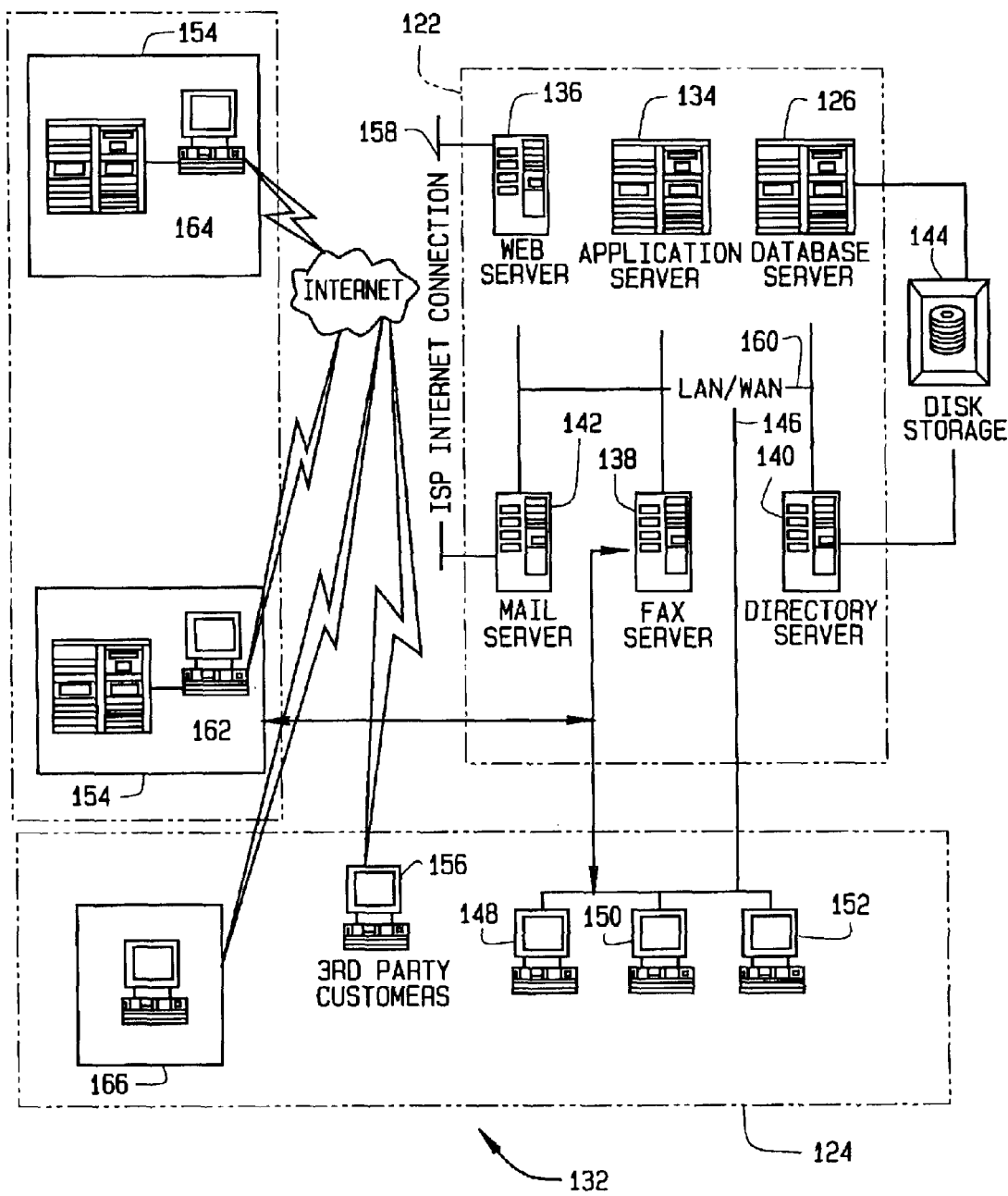
FIG. 6 is an expanded version block diagram of an exemplary embodiment of a server architecture of a system for determining the fatigue usage factor of a reactor component.

FIG. 6 is an expanded version block diagram of an exemplary embodiment of a server architecture of a system 132 for determining a fatigue usage factor of a component in a nuclear reactor. Components of system 132, identical to components of system 120 (shown in FIG. 5), are identified in FIG. 6 using the same reference numerals as used in FIG. 5. System 132 includes server sub-system 122 and user devices 124. Server sub-system 122 includes database server 126, an application server 134, a web server 136, a fax server 138, a directory server 140, and a mail server 142. A disk storage unit 144 is coupled to database server 126 and directory server 140. Servers 126, 134, 136, 138, 140, and 142 are coupled in a local area network (LAN) 146. In addition, a system administrator workstation 148, a user workstation 150, and a supervisor workstation 152 are coupled to LAN 146. Alternatively, workstations 148, 150, and 152 are coupled to LAN 146 via an Internet link or are connected through an intranet.

Each workstation 148, 150, and 152 is a personal computer having a web browser. Although the functions performed at the workstations typically are illustrated as being performed at respective workstations 148, 150, and 152, such functions can be performed at one of many personal computers coupled to LAN 146. Workstations 148, 150, and 152 are illustrated as being associated with separate functions only to facilitate an understanding of the different types of functions that can be performed by individuals having access to LAN 146.

In another embodiment, server sub-system 122 is configured to be communicatively coupled to various individuals or employees 154 and to users 156 via an ISP Internet connection 158. The communication in the exemplary embodiment is illustrated as being performed via the Internet, however, any other wide area network (WAN) type communication can be utilized in other embodiments, i.e., the systems and processes are not limited to being practiced via the Internet. In addition, and rather than a WAN 160, local area network 146 could be used in place of WAN 160.

In the exemplary embodiment, any authorized individual or an employee of the business entity having a workstation 162 can access server subsystem 122. One of user devices 124 includes a senior manager's workstation 164 located at a remote location. Workstations 162 and 164 are personal computers having a web browser. Also, workstations 162 and 164 are configured to communicate with server sub-system 122. Furthermore, fax server 138 communicates with employees located outside the business entity and any of the remotely located user systems, including a user system 166 via a telephone link. Fax server 138 is configured to communicate with other workstations 148, 150, and 152 as well.

Systems 132 and 120 determine a fatigue usage factor of a component in a nuclear reactor by following the steps of method 90 described above. Particularly, systems 132 and 120 are configured to determine a flow scaling factor for each stress component of a stress cycle, apply the flow scaling factor in rapid cycling stress conditions, and perform a fatigue evaluation by calculating the usage factor using the flow scaling factor.

While the invention has been described in terms of various specific embodiments, those skilled in the art will recognize that the invention can be practiced with modification within the spirit and scope of the claims.

What is claimed is:

1. A method for calculating a fatigue usage factor of a component in a nuclear reactor, said method comprising:

determining a flow scaling factor for each stress component of a stress cycle;

applying the flow scaling factor to rapid cycling stress conditions; and performing a fatigue evaluation by calculating a fatigue usage factor using the flow scaling factor, wherein the flow scaling factor comprises a ratio of a temperature fluctuation ratio at a first reactor operating condition divided by a temperature fluctuation ratio at a second reactor operating condition, the temperature fluctuation ratio comprising a ratio of a metal temperature range over a fluid temperature range.

2. A method in accordance with claim 1 wherein the flow scaling factor is calculated by the following:

$$SCF_f = (\Delta T_M/\Delta T_f)_{new}/(\Delta T_M/\Delta T_f)_{old}$$

where, $\Delta T_M$=Metal Temperature Range;

$\Delta T_f$=Fluid Temperature Range;

$(\Delta T_M/\Delta T_f)_{old}$=a baseline operating condition ratio; and $(\Delta T_M/\Delta T_f)_{new}$=a new operating condition ratio.

3. A method in accordance with claim 2 wherein performing a fatigue evaluation comprises:

determining scaling factors for each stress component of a stress cycle; and applying the appropriate scaling factor to the corresponding stress component of the stress cycle.

4. A method in accordance with claim 3 wherein performing a fatigue evaluation further comprises:

calculating a fatigue strength correction factor at the second reactor operating condition, $K_{e,new}$, and an elastic modulus correction factor, $E_c/E_a$; and determining an alternating stress intensity, $S_{alt,new}$, by the following:

$$S_{alt,new}=(1/2)*K_{e,new}*E_c/E_a*S_{p-p'}, \text{ where } S_{p-p'} \text{ is a stress range.}$$

5. A method in accordance with claim 4 wherein performing a fatigue evaluation further comprises:

determining the allowable number of cycles, N, of the component for each peak stress intensity corresponding to a group of cycles; and determining a fatigue usage factor from the formula:

$$U=u_1+u_2+\ldots+u_x;$$

where, $u_x=n_x/N_x$, an incremental fatigue usage factor;

$n_x$=an expected number of lifetime cycles experienced by the component; and $N_x$=allowable number of cycles.

6. A method for scaling stresses in nuclear reactor components to account for changes in reactor operating conditions, said method comprising:

determining a flow scaling factor for each stress component of a stress cycle; and applying the flow scaling factor to rapid cycling stress conditions, wherein the flow scaling factor comprises a ratio of a temperature fluctuation ratio at a first reactor operating condition divided by a temperature fluctuation ratio at a second reactor operating condition, the temperature fluctuation ratio comprising a ratio of a metal temperature range over a fluid temperature range.

7. A method in accordance with claim 6 wherein the flow scaling factor is calculated by the following:

$$SCF_f=(\Delta T_M/\Delta T_f)_{new}/(\Delta T_M/\Delta T_f)_{old}$$

where, $\Delta T_M$=Metal Temperature Range;

$\Delta T_f$=Fluid Temperature Range;

$(\Delta T_M/\Delta T_f)_{old}$=a baseline operating condition ratio; and $(\Delta T_M/\Delta T_f)_{new}$=a new operating condition ratio.

8. An apparatus for calculating a fatigue usage factor of a component in a nuclear reactor, said apparatus comprising a processor programmed to:

determine a flow scaling factor for each stress component of a stress cycle;

apply the flow scaling factor to rapid cycling stress conditions; and perform a fatigue evaluation by calculating a fatigue usage factor using the flow scaling factor, wherein the flow scaling factor comprises a ratio of a temperature fluctuation ratio at a first reactor operating condition divided by a temperature fluctuation ratio at a second reactor operating condition, the temperature fluctuation ratio comprising a ratio of a metal temperature range over a fluid temperature range.

9. An apparatus in accordance with claim 8 wherein the processor is programmed to calculate the flow scaling factor by the formula:

$$SCF_f=(\Delta T_M/\Delta T_f)_{new}/(\Delta T_M/\Delta T_F)_{old}$$

where, $\Delta T_M$=Metal Temperature Range;

$\Delta T_f$=Fluid Temperature Range;

$(\Delta T_M/\Delta T_f)_{old}$=a baseline operating condition ratio; and $(\Delta T_M/\Delta T_f)_{new}$=a new operating condition ratio.

10. An apparatus in accordance with claim 9 wherein the processor is further programmed to:

determine scaling factors for each stress component of a stress cycle; and apply the appropriate scaling factor to the corresponding stress component of the stress cycle.

11. An apparatus in accordance with claim 10 wherein the processor is further programmed to:

calculate a fatigue strength reduction factor at the second reactor operating condition, $K_{e,new}$, and an elastic modulus correction factor, $E_c/E_a$; and determine an alternating stress intensity, $S_{alt,new}$, by the following:

$$S_{alt,new}=(1/2)*K_{e,new}*E_c/E_a*S_{p-p'}, \text{ where } S_{p-p'} \text{ is a stress range.}$$

12. An apparatus in accordance with claim 11 wherein the processor is further programmed to:

determine the allowable number of cycles, N, of the component for each peak stress intensity corresponding to a group of cycles; and determine a fatigue usage factor from the formula:

$$U=u_1+u_2+\ldots+u_x;$$

where, $U_x=n_x/N_x$, an incremental fatigue usage factor;

$n_x$=an expected number of lifetime cycles experienced by the component; and $N_x$=allowable number of cycles.

* * * * *